(12) United States Patent
Pinsl-Ober et al.

(10) Patent No.: US 8,026,068 B2
(45) Date of Patent: Sep. 27, 2011

(54) USE OF SILICA MATERIAL IN AN AMPLIFICATION REACTION

(75) Inventors: Judith Pinsl-Ober, Tutzing (DE); Peter Wenzig, Munich (DE); Ralf Schoenbrunner, Moraga, CA (US); Patrick O'Donnell, Alameda, CA (US); Erich Kyger, Antioch, CA (US); Khushbeer Malhotra, Concord, CA (US); Kurt Weindel, Weilenbach-Hardt (DE); Knut Bartl, Pleasanton, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 758 days.

(21) Appl. No.: 10/337,190

(22) Filed: Jan. 6, 2003

(65) Prior Publication Data

US 2004/0014070 A1 Jan. 22, 2004

Related U.S. Application Data

(60) Provisional application No. 60/347,327, filed on Jan. 8, 2002.

(51) Int. Cl.
*C12P 19/34* (2006.01)
(52) U.S. Cl. ..................... 435/6.12; 435/91.2
(58) Field of Classification Search ................ None
See application file for complete search history.

(56) References Cited

U.S. PATENT DOCUMENTS

| | | | |
|---|---|---|---|
| 5,234,809 A | 8/1993 | Boom et al. | |
| 5,496,562 A | 3/1996 | Burgoyne | 424/488 |
| 6,090,592 A | 7/2000 | Adams et al. | |
| 2003/0087397 A1 * | 5/2003 | Klein et al. | 435/91.1 |

FOREIGN PATENT DOCUMENTS

| | | |
|---|---|---|
| DE | 19717690 A1 | 10/1998 |
| DE | 19801730 A1 | 7/1999 |
| DE | 19816137 A1 | 10/1999 |
| EP | 0288618 A1 | 11/1988 |
| EP | 0288618 B1 | 7/1993 |
| EP | 0727496 A2 | 8/1996 |
| EP | 0 389 063 | 8/1997 |
| EP | 0389063 B1 | 8/1997 |
| EP | 0727496 A3 | 9/2000 |
| EP | 1 154 443 | 11/2001 |
| EP | 1154443 A1 * | 11/2001 |
| EP | 0389063 B2 | 10/2006 |
| EP | 1466018 B1 | 10/2007 |
| JP | 2-289596 | 11/1990 |
| JP | 9322777 A | 12/1997 |
| JP | 11318497 A | 11/1999 |
| WO | 9504140 A1 | 2/1995 |
| WO | 9515970 A1 | 6/1995 |
| WO | 9605213 A1 | 2/1996 |
| WO | 9609379 A1 | 3/1996 |
| WO | 9618731 A2 | 6/1996 |
| WO | 9618731 A3 | 6/1996 |
| WO | WO 96/18731 * | 6/1996 |
| WO | 9641811 A1 | 12/1996 |
| WO | 9850782 A2 | 11/1998 |
| WO | 9850782 A3 | 11/1998 |
| WO | 9851693 A1 | 11/1998 |
| WO | 9916781 A2 | 4/1999 |
| WO | 9916781 A3 | 4/1999 |
| WO | 9939010 A1 | 8/1999 |
| WO | WO 99/39010 | 8/1999 |
| WO | 0032762 A1 | 6/2000 |
| WO | 0114590 A2 | 3/2001 |
| WO | 0114590 A3 | 3/2001 |
| WO | WO 01/14590 | 3/2001 |
| WO | WO 01/14590 A2 * | 3/2001 |
| WO | 0137291 A1 | 5/2001 |
| WO | WO01/37291 A1 | 5/2001 |
| WO | 03057910 A2 | 7/2003 |
| WO | 03057910 A3 | 7/2003 |
| WO | 03058649 A1 | 7/2003 |
| WO | WO 03/058649 | 7/2003 |

OTHER PUBLICATIONS

Palmer, J., et al, 2001, "Sources of false positive *Aspergillus* DNA by PCR from normal human blood", *Abstract, Interscience Conference on Antimicrobial Agents and Chemotherapy*, BIOS Online No. PREV200200509367.

Andreadis, Joanne D., et al., 2000, "Use of immobilized PCR primers to generate covalently immobilized DNAs for in vitro transcription/translation reactions", Nucleic Acids Research, 28(2):e5i-viii.

Bartl, Knut, et al., 1998, "Simple and Broadly Applicable Sample Preparation by Use of Magnetic Glass Particles", Clin Chem Lab Med, 36(8):557-569.

Chungue, Eliane, et al., 1993, "Ultra-Rapid, Simple, Sensitive, and Economical Silica Method for Extraction of Dengue Viral RNA From Clinical Specimens and Mosquitoes by Reverse Transcriptase-Polymerase Chain Reaction", Journal of Medical Virology, 40:142-145.

Kreader, Carol A., 1996, "Relief of Amplification Inhibition in PCR with Bovine Serum Albumin or T4 Gene 32 Protein", Applied and Environmental Microbiology, 62(3):1102-1106. Rudi, Knut, et al., 1998, "Detection of Toxin-Producing *Cyanobacteria* by Use of Paramagnetic Beads for Cell Concentration and DNA Purification", Applied and Environmental Microbiology, 64(1):34-37.

Stacy-Phipps, Sandrina, et al., 1995, "Multiplex PCR Assay and Simple Preparation Method for Stool Specimens Detect Enterotoxigenic *Escherichia coli* DNA during Course of Infection", 33(5)1054-1059.

Tano, Hiroyuki, et al., 1995, "Prior Enrichment of Human Immunodeficiency Virus DNA with Probe DNA Particles for Efficient PCR Diagnosis", Journal of Clinical Microbiology, 33(9):2489-2491.

(Continued)

*Primary Examiner* — Kenneth R. Horlick

(74) *Attorney, Agent, or Firm* — Charles M. Doyle; Olga Kay

(57) ABSTRACT

This invention relates to a method for the isolation of a target nucleic acid using a material with an unmodified silica surface and subsequent amplification of the target nucleic acid in the presence of the material with an unmodified silica surface. The method is preferably carried out as an automated process preferably in a high throughput format. The method is preferably used in diagnostics.

11 Claims, 2 Drawing Sheets

OTHER PUBLICATIONS

Rompp, Hermann, 1966, "Chemie Lexikon", Franckh'sche Verlagshandlung Stuttgart, 2415-2418.

Wijnen, Peter W. J. G., et al., 1991, "Silica Gel from Water Glass: a SAXS Study of the formation and ageing of Fractual Aggregates", J. Appl. Cryst., 24:759-764.

Grant, Richard P., 2002, "Whither Bionet?", The Biochemist, 51-52.

ROMPP Online, Version 3.1, 2003, "Glas", ID=RD-07-01164, http://www.roempp.com/prod/roempp.php.

Gilbert, Don, 2004, "Software Review: Bioinformatics Software Resources", Briefings in Bioinformatics, 5 (3):300-304.

"The Biosci Electronic Newsgroup Network Information Sheet", 1-11, Last revised 2006, http://www.bio.net/docs/biosci-info.txt.

ROMPP Online, Thieme Chemistry, "Neues Update Online", http://www.roempp.com/de/formate/encyclopedias/roempp/format/roempp-online.html, (2009).

ROMPP Online, Thieme Chemistry, http://roempp.com/en/products/encyclopedias/roempp.html, (2010).

* cited by examiner

USE OF SILICA MATERIAL IN AN AMPLIFICATION REACTION

This application claims the benefit of priority under 35 U.S.C. §119(e) of U.S. Provisional Application No. 60/347,327, filed Jan. 8, 2002, the contents of which are hereby incorporated by reference therein.

BACKGROUND OF THE INVENTION

1. Field of the Invention

This invention relates to a method for the isolation of nucleic acids using a material with an unmodified silica surface, such as magnetic glass particles, and subsequent amplification of a target nucleic acid in the presence of the material with an unmodified silica surface. The method is preferably carried out as an automated process preferably in a high throughput format. The method is preferably used in diagnostics.

2. Background Art

Many biological substances, especially nucleic acids, present special challenges in terms of isolating them from their natural environment. On the one hand, they are often present in very small concentrations and, on the other hand, they are often found in the presence of many other solid and dissolved substances e.g. after lysis of cells. This makes them difficult to isolate or to measure, in particular in biospecific assays which allow the detection of specific analytes, e.g. nucleic acids, or specific analyte properties and play a major role in the field of diagnostics and bioanalytics in research and development.

Before a biological substance or compound, for example a nucleic acid, can be analyzed in a biospecific assay or used for other processes, it often must be isolated or purified from biological samples containing complex mixtures of different components as e.g. proteinaceous and non-proteinaceous components. Frequently, the biological substance is contained in a bacterial cell, a fungal cell, a viral particle, or the cell of a more complex organism, such as a human blood cell or a plant cell. The biological substance to be analyzed is also frequently called substance of interest or target substance. Frequently, the target substance is a nucleic acid which is therefore called a target nucleic acid.

To release the contents of said cells or particles, they may be treated with enzymes or with chemicals to dissolve, degrade or denature the cell walls and/or cell membranes. This process is commonly referred to as lysis. The resulting solution containing such lysed material is referred to as lysate. A problem often encountered during the lysis is that enzymes degrading the substance of interest, e.g. deoxyribonucleases or ribonucleases degrading nucleic acids, come into contact with the substance of interest during lysis. These degrading enzymes may be present outside the cells or may have been spatially separated in different cellular compartments before the lysis. Other components released during this process might include, for example, endotoxins belonging to the family of lipopolysaccharides which are toxic to cells and can cause problems for products intended to be used in human or animal therapy. There are a variety of means to tackle this problem mentioned-above. It is common to use chaotropic agents as e.g. guanidinium salts or anionic, cationic, zwitterionic or non-ionic detergents when nucleic acids are intended to be set free. It is also an advantage to use proteases, e.g. proteinase K, which rapidly degrade these enzymes or unwanted proteins. However, this may produce another problem as the said substances or enzymes can interfere with reagents or components in subsequent steps.

If the substances of interest are nucleic acids, they are normally extracted and thus separated from the complex lysis mixtures before they are used in an assay. There are several methods for the extraction of nucleic acids as sequence-dependent or biospecific methods (affinity chromatography, hybridisation to immobilised probes) or sequence-independent or physico-chemical methods (liquid-liquid extraction with e.g. phenol-chloroform, precipitation with e.g. pure ethanol, extraction with filter paper, extraction with micelle-forming agents as cetyl-trimethyl-ammonium-bromide, binding to immobilised, intercalating dyes, e.g. acridine derivatives, adsorption to silica gel or diatomic earths, adsorption to magnetic glass particles (MGPs) or organo silane particles under chaotropic conditions. Extraction using solid phases usually comprises the steps of adding the lysate to the solid phase under conditions allowing binding of the substance of interest to the solid phase, removal of the remainder of the lysate from the solid phase bound substance and subsequent release of the substance of interest from the solid phase into a liquid eluate (sometimes called elution). The result of the extraction process is usually a solution containing the substance of interest in dissolved state. Particularly interesting for extraction purposes is the adsorption of nucleic acids to a glass surface, in particular the glass surfaces of MGPs. Many procedures for isolating nucleic acids from their natural environment have been proposed in recent years by the use of their binding behavior to glass surfaces.

After the extraction step, the solution containing the substance of interest, e.g. the nucleic acid, is analyzed in a biospecific assay to show whether the substance of interest was present in the original sample. Examples for biospecific assays are hybridization assays for nucleic acids, immuno assays or receptor-ligand assays for proteins. Hybridization assays use the specific base-pairing for the molecular detection of nucleic acid analytes, for example, RNA or DNA. Hence, for example, oligonucleotide probes with sequence of a length of about 18 to about 20 nucleotides may enable the specific recognition of a selected complementary sequence, for example, in the human genome. Another assay which entails the selective binding of two oligonucleotide primers is the polymerase chain reaction (PCR) described in U.S. Pat. No. 4,683,195. This method allows the selective amplification of a specific nucleic acid region to detectable levels by a thermostable polymerase in the presence of desoxynucleotide triphosphates in several cycles. Afterwards the nucleic acid is detected by means known to the person skilled in the art. Other methods, such as the TAQMAN® assay disclosed in WO92/02638, allow the simultaneous amplification and detection of a nucleic acid of interest.

Normally the lysis, extraction and amplification steps are performed consecutively while a variety of different operations have to be carried out, e.g. removal of only protein containing phases, elution of the nucleic acids from the carried used for extraction and removal of the carrier, transfer of liquids into fresh tubes and so on. New methods of preparing nucleic acid samples are needed to improve the efficiency and/or sensitivity of, for example, nucleic acid detection methods.

SUMMARY OF THE INVENTION

The present invention provides methods of carrying out sample preparation followed by nucleic acid amplification that provide improvements in reaction efficiency and detection sensitivity while reducing the manipulation steps required. In the methods of the present invention, sample preparation is carried out using an unmodified glass surface, preferably consisting of magnetic glass particles, to capture nucleic acid contained in the sample, and the resulting glass-nucleic acid complex is combined directly with the amplification reaction reagents and subject to amplification conditions. A critical aspect of the invention is that the amplification is carried out in the presence of the glass particles.

The methods of the present invention provide several advantages over previously described methods using magnetic glass particles. An advantage is that the methods require less manipulation steps, which results in a decrease in time and effort required and allows for improved automation. Most surprisingly, the present methods provide improved reaction sensitivity compared to methods in which the purified nucleic acid is eluted from the glass prior to amplification and the amplification is carried out not in the presence of the glass.

Therefore, the present invention contemplates a method for the purification and amplification of a target nucleic acid from a biological sample comprising said target nucleic acid, said method comprising the steps of adding a material comprising an unmodified silica surface to said sample to bind said target nucleic acid to said material, eluting said target nucleic acid from said material, amplifying said target nucleic acid, wherein amplification is carried out in the presence of said material in said sample. The method further contemplates a method for the amplification of a target nucleic acid in a sample, said method comprising the steps of adding a material comprising an unmodified silica surface to said sample, amplifying said target nucleic acid, wherein amplification is carried out in the presence of said material in said sample.

The target nucleic acid may be a deoxyribonucleic acid (DNA) or a ribonucleic acid (RNA) and is preferably amplified with, for example, the polymerase chain reaction (PCR). The glass beads are preferably magnetic glass particles. They are preferably manufactured by the sol-gel-method, most preferably using a spray-drying step with a two-nozzle spray drier operated under specific conditions. Preferably, the method is automated or performed in a high-throughput format. Most preferably, the method is used in diagnostics or for the screening of blood for the presence of a target nucleic acid from a virus.

DETAILED DESCRIPTION OF THE INVENTION

Figure 1:
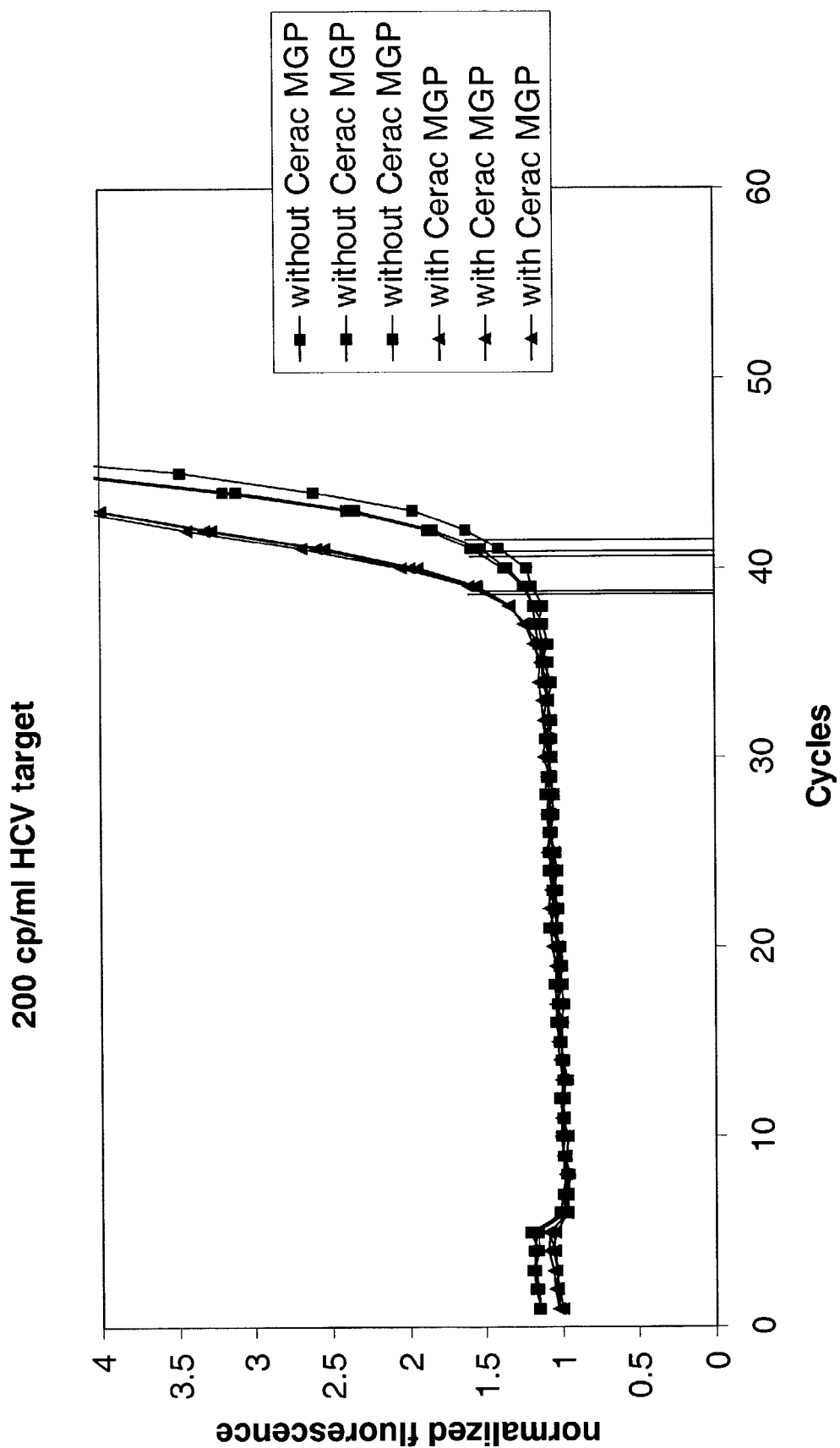
FIG. 1: Comparison of the $C_T$-values of PCR reactions with and without magnetic glass particles containing the pigment manufactured by the company CERAC and manufactured according to EP 1154443 (cp/ml: copies/ml).

The term "unmodified" shall mean that there is no further chemical modification, i.e. no other chemical groups are attached covalently or non-covalently. The term "unmodified silica surface" shall mean that no other chemical groups are attached covalently or non-covalently which serve as an intermediary substance for nucleic acid binding and where the nucleic acids bind to the intermediary substance and not to the silica surface itself. Therefore, the nucleic acids are capable of binding by hydrogen bonding and other atomic forces directly to the "unmodified silica surface" in the presence of, for example, high salt concentrations. An example of a modified surface are silica surfaces to which oligonucleotides are attached which bind in sequence-specific manner nucleic acid molecules. Another example for modified silica surfaces are silica surfaces coated with streptavidin which binds to biotinylated DNA molecules.

According to the present invention, a "target nucleic acid" shall be the nucleic acid of interest or more generally substance of interest, i.e. a nucleic acid which shall be investigated as its presence is indicative of a certain condition or disease of a human or animal. For example, the presence of a nucleic acid from a virus (e.g. from hepatitis B virus, hepatitis C virus or human immunodeficiency virus) indicates that the respective individual is infected by the respective virus. In consequence, this nucleic acid from this specific virus would be the target nucleic acid. Other target nucleic acids are e.g. nucleic acids which are indicative of a predisposition of an individual to a certain disease, e.g. an inherited disease as sickle cell anemia, or to certain types of cancer.

The present invention contemplates a method for the purification and amplification of a target nucleic acid from a biological sample comprising said target nucleic acid, said method comprising the steps of adding a material comprising an unmodified silica surface to said sample to bind said target nucleic acid to said material, eluting said target nucleic acid from said material, amplifying said target nucleic acid, wherein amplification is carried out in the presence of said material in said sample. Preferably more than 50%, more preferably more than 80% or even 100% of the material comprising an unmodified silica surface which is used for binding the target nucleic acid thereto is present in the sample during amplification of the target nucleic acid. It is also evident to the person skilled in the art that because of the advantages described above the material comprising an unmodified silica surface may be directly added to an amplification mixture to enhance the sensitivity. Therefore, the invention also contemplates a method for the amplification of a target nucleic acid in a sample, said method comprising the steps of adding a material comprising an unmodified silica surface to said sample, amplifying said target nucleic acid, wherein amplification is carried out in the presence of said material in said sample. The conditions during amplification in both methods according to the invention are chosen in such a manner that no target nucleic acid is bound to the material comprising an unmodified silica surface. However, a small percentage of the target nucleic acid may be bound resulting from unspecific binding which cannot be totally excluded. Both methods may further comprise the step of detecting the amplified target nucleic acid. In a preferred embodiment of the invention the target nucleic acid is RNA or DNA. Preferably, amplification conditions are chosen so that the primers and/or the template do not bind the material.

In an embodiment of the invention, the biological sample comprises viruses or bacterial cells, as well as isolated cells from multicellular organisms as e.g. human and animal cells such as leucocytes, and immunologically active low and high molecular chemical compounds such as haptens, antigens, antibodies and nucleic acids, blood plasma, cerebral fluid, sputum, stool, biopsy specimens, bone marrow, oral rinses, blood serum, tissues, urine or mixtures thereof. In a preferred embodiment of the invention the biological sample is a fluid from the human or animal body. Preferably the biological sample is blood, blood plasma, blood serum or urine. The blood plasma is preferably EDTA-, heparin- or citrate-treated blood plasma. In an embodiment of the invention the biological sample comprises bacterial cells, eukaryotic cells, viruses or mixtures thereof. In a preferred embodiment of the invention, the virus is the hepatitis A virus (HAV), hepatitis B virus (HBV), hepatitis C virus (HCV), the human immunodeficiency virus (HIV), the human papilloma virus (HPV) or parvovirus B19. The biological sample can also be of a type used for environmental analysis, food analysis or molecular biology research, e.g. from bacterial cultures or phage lysates. The biological sample comprising a mixture of biological compounds comprising non-target and a target nucleic acid needs not to be lysed, when the biological sample can be used without pretreatment in the method according to the invention. However, preferably a biological sample comprising non-target nucleic acids and a target nucleic acid is lysed to create a mixture of biological compounds comprising non-target and a target nucleic acid. Therefore, the biological compounds, non-target nucleic acids and the target nucleic acid contained in the biological sample are released thereby creating a mixture of biological compounds comprising non-target nucleic acids and the target nucleic acid. Procedures for lysing biological samples are known by the expert and can be chemical, enzymatic or physical in nature. A combination of these procedures is applicable as well. For instance, lysis can be performed using ultrasound, high pressure, shear forces, alkali, detergents or chaotropic saline solutions, or proteases or lipases. For the lysis procedure to obtain nucleic acids, special reference is made to Sambrook et al.: Molecular Cloning, A Laboratory Manual, 2nd Addition, Cold Spring Harbour Laboratory Press, Cold Spring Harbour, N.Y. and Ausubel et al.: Current Protocols in Molecular Biology 1987, J. Wiley and Sons, NY.

The method according to the invention comprises the step of adding a material comprising an unmodified silica surface to said sample to bind said target nucleic acid to said material. The material with an unmodified silica surface can be e.g. glass fibers, diatomaceous earth, glass beads or particles, or magnetic glass particles or other substances covered with an unmodified glass surface. The conditions for this are basically known to the expert in the field. These processes are described in detail by various documents. In Proc. Natl. Acad. USA 76, 615-691 (1979), for instance, a procedure for binding nucleic acids from agarose gels in the presence of sodium iodide to ground flint glass is proposed. The purification of plasmid DNA from bacteria on glass dust in the presence of sodium perchlorate is described in Anal. Biochem. 121 (1982) 382-387. In DE-A 37 34 442, the isolation of single-stranded M13 phage DNA on glass fiber filters by precipitating phage particles using acetic acid and lysis of the phage particles with perchlorate is described. The nucleic acids bound to the glass fiber filters are washed and then eluted with a methanol-containing Tris/EDTA buffer. A similar procedure for purifying DNA from lambda phages is described in Anal. Biochem. 175 (1988) 196-201. The procedure entails the selective binding of nucleic acids to glass surfaces in chaotropic salt solutions and separating the nucleic acids from contaminants such as agarose, proteins or cell residue. To separate the glass particles from the contaminants, the particles may be either centrifuged or fluids are drawn through glass fiber filters. This is a limiting step, however, that prevents the procedure from being used to process large quantities of samples. In a preferred embodiment of the invention, magnetic glass particles are used to immobilize nucleic acids after precipitation by adding salt and ethanol as described e.g. in Anal. Biochem. 201 (1992) 166-169 and PCT GB 91/00212.

The procedure for binding the target nucleic acid (and also the non-target nucleic acids) to glass particles can be described in detail as follows. It is preferably performed in the presence of chaotropic salts with a concentration of between 1 and 8 mol/l, and preferably between 2 and 6 mol/l. Chaotropic salts can be sodium iodide, sodium perchlorate, guanidinium thiocyanate, guanidinium isothiocyanate or guanidinium hydrochloride. A chaotropic agent according to the present invention is any chemical substance which disturbs the ordered structure of liquid water and has the effect that DNA or RNA binds to the magnetic glass particles if this agent is present in the DNA or RNA containing solution. Other biological substances known to the expert in the field may also be present. Still other substances are also possible. The purification effect results from the behavior of DNA or RNA to bind to material with a glass surface under these conditions i.e. in the presence of certain concentrations of a chaotropic agent, higher concentrations of organic solvents or under acidic conditions. To bring the mixture of biological compounds comprising non-target nucleic acids and the target nucleic acid, the glass beads with an unmodified glass surface are added to the mixture and incubated for a period of time sufficient for the binding to occur. Experts are usually familiar with the duration of the incubation step. This step can be optimized by determining the quantity of immobilized nucleic acids on the surface at different points in time. Incubation times of between 10 seconds and 30 minutes can be appropriate for nucleic acids. After incubation, the non-target nucleic acids and the target nucleic acid are separated from the liquid. This may be achieved in general by gravity or in the convenient case of nucleic acids bound to magnetic glass particles by separating the material bound to the magnetic particles by applying a magnetic field. For instance, the magnetic particles can be pulled to the wall of the vessel in which incubation was performed. The liquid containing the biological compounds that were not bound to the magnetic particles can then be removed. Therefore, the method according to the invention contains the step of separating said material with said bound non-target nucleic acids and said bound target nucleic acid from the non-bound biological compounds. The removal procedure used depends on the type of vessel in which incubation was performed. Suitable steps include removing the liquid via pipeting or aspiration. The material with the bound DNA or RNA may then be washed at least once, preferably with a mixture of 70 volume parts ethanol with 30 volume parts water ("70% Ethanol") or in an acidic wash solution as described in WO 99/40098. A wash solution is used that does not cause the nucleic acids and the target nucleic acid to be released from the material surface but that washes away the undesired contaminants as thoroughly as possible. This wash step preferably takes place by incubating the glass beads with the unmodified silica surface with the bound nucleic acids and the target nucleic acid. The material is preferably resuspended during this step. The contaminated wash solution is preferably removed just as in the binding step described above. After the last wash step, the material can be dried briefly in a vacuum, or the fluid can be allowed to evaporate. A pretreatment step using acetone may also be performed.

In certain embodiments, the invention further comprises the step of eluting said bound non-target nucleic acids and said bound target nucleic acid from said material and amplifying said target nucleic acid afterwards. For elution to take place, the material with the unmodified silica surface is resuspended in a solution with no or only a low amount of chaotropic agent and/or organic solvent. Alternatively, the suspension can be diluted with a solution with no or only a low amount of chaotropic agent and/or organic solvent. Buffers of this nature are known from DE 3724442 and Analytical Biochemistry 175 (1988) 196-201. The elution buffers with a low salt content are in particular buffers with a content of less than 0.2 mol/l. In an especially preferred embodiment, the elution buffer contains the substance Tris for buffering purposes, in particular a Tris buffered solution with a pH around 7 or above 7. In another special embodiment, the elution buffer is demineralized water. The solution containing the purified target nucleic acid is now ready to be used in the amplification reaction, i.e. the solution with the non-target nucleic acids and the target nucleic acid and the material with the unmodified silica surface are transferred to a new reaction tube containing all reagents necessary for amplification. Otherwise, a solution containing all reagents necessary for amplification is added to the suspension of the material with the unmodified silica surface and the released non-target nucleic acids and the target nucleic acid.

In other embodiments, the material with the unmodified silica surface and the bound target nucleic acids can be brought under conditions in which the target nucleic acids can be amplified, as described below, without a separate elution step. In such embodiments, the amplification conditions can be chosen so that the target nucleic acid can be released from the material with the unmodified silica surface to facilitate amplification. Preferably, amplification conditions are chosen so that primers do not bind to the material with the unmodified silica surface.

Generally speaking, for washing and binding steps, preferably liquids are used which are suitable for processes in molecular biology, in particular deoxyribonucleic acid (DNA) or ribonucleic acid (RNA) purification processes which make use of the binding of these substances to glass particles under certain conditions. Preferred liquids comprise alcohols and/or ketones or any mixtures thereof with water. Alcohols shall include according to the invention preferably primary, secondary or tertiary alcohols of the general formula R-OH where the R stands for the general formula —(—CH$_2$)$_n$—CH$_3$ with n>=0. However, other alcohols can also be used if they are suitable for molecular biology purposes as e.g. glycerol. Particularly suitable are the alcohols isopropanol, ethanol or mixtures thereof with water, preferably a mixture of 80 volume parts of isopropanol with 20 volume parts of water. In another embodiment of the invention the liquid comprises ketones as e.g. acetone. Further, suitable aqueous buffered solutions are used. Buffer systems which are suitable for molecular biology purposes may be found e.g. in Sambrook, et al., Molecular Cloning, Cold Spring Harbor University Press (1989). Preferred buffer substances are Tris-hydroxymethylamine (TRIS), phosphate, N-(2-hydroxy-ethyl) piperazine-N'-(2-ethanesulfonic acid) (HEPES), salts thereof or other suitable substances. Additionally, substances may be present which modify the ionic strength of the solution as e.g. NaCl, KCl or CaCl$_2$ or which are metal cation complexing agents as e.g. ethylene-diamine-tetra-acetic acid (EDTA) or the salts thereof.

The method according to the present invention is suitable for the purification of nucleic acids, i.e. RNA or DNA, from complex mixtures with other biological compounds containing them. Thereby, also mixtures of different nucleic acids may be purified, even mixtures containing a target nucleic acid in low abundance. In one embodiment of the invention mixtures of specific nucleic acids are purified, in which the target nucleic acid(s) may be a minor component in terms of concentration (or may be present in low abundance).

In a preferred embodiment of the invention, the target nucleic acid is amplified with the polymerase chain reaction (PCR). The amplification method may also be the ligase Chain Reaction (LCR, Wu and Wallace, Genomics 4 (1989) 560-569 and Barany, Proc. Natl. Acad. Sci. USA 88 (1991) 189-193); Polymerase Ligase Chain Reaction (Barany, PCR Methods and Applic. 1 (1991)5-16); Gap-LCR (PCT Patent Publication No. WO 90/01069); Repair Chain Reaction (European Patent Publication No. EP 439,182 A2), 3SR (Kwoh, et al., Proc. Natl. Acad. Sci. USA 86 (1989)1173-1177; Guatelli, et al., Proc. Natl. Acad. Sci. USA 87 (1990)1874-1878; PCT Patent Publication No. WO 92/0880A), and NASBA (U.S. Pat. No. 5,130,238). Further, there are strand displacement amplification (SDA), transciption mediated amplification (TMA), and Qβ-amplification (for a review see e.g. Whelen and Persing, Annu. Rev. Microbiol. 50 (1996) 349-373; Abramson and Myers, Current Opinion in Biotechnology 4 (1993)41-47).

In a preferred embodiment, the method may further comprise the step of detecting the amplified target nucleic acid. The amplified target nucleic acid may be determined or detected by standard analytical methods known to the person skilled in the art and described e.g. in Sambrook, et al., Molecular Cloning, Cold Spring Harbor University Press (1989), Lottspeich and Zorbas (eds.), "Bioanalytik" (1st edition 1998), Spektrum Akademischer Verlag, Heidelberg, Berlin, Germany, or in Ausubel, et al., Current Protocols in Molecular Biology (1987), J. Wiley and Sons, N.Y., USA. There may be also further purification steps before the target nucleic acid is detected e.g. a precipitation step. The detection methods may include but are not limited to the binding or intercalating of specific dyes as ethidiumbromide which intercalates into the double-stranded DNA and changes its fluorescence thereafter. The purified nucleic acids may also be separated by electrophoretic methods optionally after a restriction digest and visualized thereafter. There are also probe-based assays which exploit the oligonucleotide hybridization to specific sequences and subsequent detection of the hybrid. It is also possible to sequence the target nucleic acid after further steps known to the expert in the field. Other methods apply a diversity of nucleic acid sequences to a silicon chip to which specific probes are bound and yield a signal when a complementary sequences bind.

In a particularly preferred embodiment of the invention, the target nucleic acid is detected by measuring the intensity of fluorescence light during amplification. This method entails the monitoring of real time fluorescence. A particularly preferred method exploiting simultaneous amplification and detection by measuring the intensity of fluorescent light is the TAQMAN® method disclosed in WO92/02638 and the corresponding U.S. Pat. Nos. 5,210,015, 5,804,375, 5,487,972. This method exploits the exonuclease activity of a polymerase to generate a signal. In detail, the target nucleic acid is detected by a process comprising contacting the sample with an oligonucleotide containing a sequence complementary to a region of the target nucleic acid and a labeled oligonucleotide containing a sequence complementary to a second region of the same target nucleic acid strand, but not including the nucleic acid sequence defined by the first oligonucleotide, to create a mixture of duplexes during hybridization conditions, wherein the duplexes comprise the target nucleic acid annealed to the first oligonucleotide and to the labeled oligonucleotide such that the 3'-end of the first oligonucleotide is adjacent to the 5'-end of the labeled oligonucleotide. Then this mixture is treated with a template-dependent nucleic acid polymerase having a 5' to 3' nuclease activity under conditions sufficient to permit the 5' to 3' nuclease activity of the polymerase to cleave the annealed, labeled oligonucleotide and release labeled fragments. The signal generated by the hydrolysis of the labeled oligonucleotide is detected and/or measured. TAQMAN® technology eliminates the need for a solid phase bound reaction complex to be formed and made detectable. In more general terms, the amplification and/or detection reaction of the method according to the invention is a homogeneous solution-phase assay. A further preferred method is in the LIGHTCYCLER™ format (see e.g. U.S. Pat. No. 6,174,670).

In a preferred embodiment of the present invention, the method is automated, i.e. the method carries out an automatable process as e.g. described in WO 99/16781. Automatable process means that the steps of the process are suitable to be carried out with an apparatus or machine capable of operating with little or no external control or influence by a human being. Automatized method means that the steps of the automatable method are carried out with an apparatus or machine capable of operating with little or no external control or influence by a human being. Only the preparation steps for the method may have to be done by hand, e.g. the storage containers have to filled up and put into place, the choice of the samples has to be done by a human being and further steps known to the expert in the field, e.g. the operation of the controlling computer. The apparatus or machine may e.g. add automatically liquids, mix the samples or carry out incubation steps at specific temperatures. Typically, such a machine or apparatus is a robot controlled by a computer which carries out a program in which the single steps and commands are specified. In a preferred embodiment of the invention, the method is in a high-throughput format, i.e. the automated methods is carried out in a high-throughput format which means that the methods and the used machine or apparatus are optimized for a high-throughput of samples in a short time. In a very preferred embodiment of the invention, the material with an unmodified silica surface comprises glass beads with an unmodified glass surface.

These glass beads were described above and belong to the state of the art. In a very preferred embodiment of the invention, the material with an unmodified silica surface comprises magnetic glass particles with an unmodified glass surface. The magnetic glass particles are a solid dispersion of small magnetic cores in glass, i.e. they are glass droplets in which very small magnetic objects are dispersed. Those objects that are referred to as magnetic are drawn to a magnet, i.e. ferri- or ferromagnetic or superparamagnetic materials for instance. Paramagnetic substances are not useful as they are only drawn to a magnetic very weakly which is not sufficient for a method according to this invention. Preferred are ferr- or ferromagnetic materials, in particular if they have not yet been premagnetized. Premagnetization in this context is understood to mean bringing in contact with a magnet, which increases the remanence. Preferred magnetic materials are iron or iron oxide as e.g. magnetite ($Fe_3O_4$) or $Fe_2O_3$, preferably $\gamma$-$Fe_2O_3$. In principle, barium ferrite, nickel, cobalt, Al—Ni—Fe—Co alloys or other ferri- or ferromagnetic material could be used. Particularly preferred according to the present invention are the magnetic glass particles described in WO96/41811 or WO 00/32762.

In a very preferred embodiment of the invention, the magnetic glass particles with an unmodified glass surface have a low iron leach which is essential for the method according to the invention when using magnetic glass particles, as iron is an inhibitor of the subsequent amplification reaction, i.e. iron is an enzymatic inhibitor. Therefore, this is an important feature of the magnetic glass particles with an unmodified glass surface.

In the most preferred embodiment of the invention, the magnetic glass particles with an unmodified surface are those described in the European application EP 00110165.8 which are also publicly available in the MagNA Pure LC DNA Isolation Kit I (Roche, Mannheim, Germany). These particles sediment slowly and can therefore be advantageously used in an automated method according to the invention. The production thereof is summarized below.

The magnetic glass particles are substantially spherical and have a small diameter and contain at least one magnetic object with a diameter between 5 and 500 nm. This has surprising consequences on the sedimentation kinetics, quantified by the half time values $t_{1/2}$, which is the time span until 50% of the particles have sedimented from a specific volume element. The half-life period for the sedimentation of a 3 mg/ml weight-per-volume suspension of the MGPs with an unmodified glass surface according to the invention in isopropanol is more than 3 min, preferably 4 min, more preferably 6 min. However the most preferred values for the half-life period is more than 10 min or even more than 20 min. The magnetic objects of the most preferred MGPs may be e.g. a magnetic pigment. The size of the magnetic objects is in the nanoscale range, i.e. between 5 to 500 nm, preferably between 10 to 200 nm, most preferably between 15 to 50 nm. Suitable magnetic pigments are manufactured by the company CERAC which have a mean diameter of 23 nm and consist of $\gamma$-$Fe_2O_3$ (BET-surface 50 $m^2$/g, CERAC: P.O. Box 1178, Milwaukee, Wis. 53201-1178 USA; Article-No. I-2012). The most preferred magnetic glass particles according to the present invention are further characterized by the fact that the MGPs have a particle diameter between 0.5 μm and 5 μm, preferably between 1 μm to 2 μm as determined by high resolution scanning electron microscopy, whereas the magnetic objects have a diameter between 5 to 500 nm, preferably between 10 to 200 nm, most preferably in the range of 15 to 50 nm as described above. Hence, the MGPs are further characterized by a diameter ratio of magnetic pigment core to magnetic glass particle of less than 1 to 10 as determined by high resolution scanning electron microscopy The most preferred MGPs are microporous but have a highly-structured and therefore relatively large surface with more than 6 $m^2$/g. Preferably, the magnetic glass particles have a surface area in the range of 5 to 100 $m^2$/g, preferably 5 to 90 $m^2$/g, more preferably in the range of 10 to 50 $m^2$/g, most preferably in the range of 15 to 30 $m^2$/g. This can be determined by the Braunauer-Emett-Teller-method using an automated commercial apparatus. For a discussion of this method, familiarly called the BET method, see S. Braunauer, The Adsorption of Gases and Vapors, Princeton University Press 1 1943).

The magnetic glass particles used in the present invention may be provided in different formulations essentially as described in European patent publication EP1154443, the content of which is hereby incorporated by reference in its entirety. It is possible to provide them in the form of a tablet, as a powder or preferably as a suspension. In a preferred embodiment of the invention these suspensions contain between 5 to 60 mg/ml magnetic glass particles (MGPs). In another embodiment of the invention the silica-containing material is suspended in aqueous buffered solutions which may optionally contain a chaotropic agent in a concentration of between 2 and 8 mol/l, and preferably between 4 and 6 mol/l. Chaotropic salts are sodium iodide, sodium perchlorate, guanidinium thiocyanate, guanidinium isothiocyanate or guanidinium hydrochloride. A chaotropic agent according to the present invention is any chemical substance which will disturb the ordered structure of liquid water and will have the effect that DNA or RNA will bind to the MGPs according to the present invention if this agent is present in the DNA or RNA containing solution. Other compounds known to the expert in the field are also possible.

In a preferred embodiment of the invention, the magnetic glass particles with an unmodified glass surface are manufactured by the sol-gel method described in EP1154443 and WO 96/41811, in particular wherein the sol-gel method comprises the steps of:
(a) suspending magnetic objects in a sol
(b) hydrolyzing the sol to cover the magnetic objects with a gel
(c) spray-drying the magnetic objects covered with a gel in a two-nozzle spray-drier, and
(d) sintering the spray-dried powder to form a glass from the gel covering the magnetic objects.

The most preferred MGPs according to the invention are manufactured according to the international application EP1154443 which are also provided in the MagNA Pure LC DNA Isolation Kit I (Roche, Mannheim, Germany)). They are also produced by the sol-gel-method as described in the international application (EP1154443) using magnetic objects or pigments with a diameter of about 23 nm (manufactured by CERAC consisting of $\gamma$-$Fe_2O_3$; CERAC: P.O. Box 1178, Milwaukee, Wis. 53201-1178 USA; Article-No. I-2012). After the magnetic objects are covered with a gel, a powder is created by spraying the slurry through a two-fluid nozzle. Suitable spray-drying systems are produced by Nubilosa Molekularzerstaubung, Ladisch GmbH & Co. KG, Konstanz, Germany, e.g. the "Labor-Zerstäubungstrockner (Typ LTK)" or by Büchi A G, Uster, Switzerland, e.g. the Mini Spray Dryer (Type B-191). Because of the diameter ratios of magnetic cores to the glass shell are less than 1 to 10, preferably between 1:10 and 1:1000, the geometry and the number of incorporated magnetic cores or of their inert carriers do not determine shape and size of the particles but the conditions of manufacturing, in particular the conditions during spray drying. In other words, the choice of pressure, inlet temperature, outlet temperature and flow rate during the spray drying procedure are the degrees of freedom which determines the size distribution, the shape of the glass drops and thereby will modify the MGPs. Therefore, the nozzles of the spray-drying system are heated. The inlet temperature is between 120° C. and 500° C., preferably between 170° C. and 230° C. or 150° C. and 230° C., most preferably between 150° C. and 200° C. or 190° C. and 210° C. or at 200° C. or slightly less. The outlet temperature depends on the boiling point of the sol and thereby on the solvent and may be above, equal or slightly under, i.e. less than 10° C., the boiling point of the solvent. When ethanol is used as solvent, it is between 50° C. and 300° C., preferably 70° C. and 150° C., most preferably between 80° C. and 110° C. The optimal temperature is between 90° C. to 100° C. The nozzle pressure is more than 3 bar, preferably it is regulated to 4 to 6 bar. The artisan will appreciate the fact that the exact parameters will depend on the spray-drying system used. However, he can transfer the teachings of the present invention to any other spray-drying system and find out the parameters by taking the disclosures of this invention into account. Formulas as described in Masters: Spray Drying Handbook, Fifth Edition, John Wiley & Sons (1991) New York can lead him the way to find out which parameters have to be chosen for another setting. Preferably, he will question the manuals of his spray-drying system or contact the technical service of the spray-drying system manufacturer.

To optimize the yield, the densification or sinter temperature should be as high as possible, i.e. slightly below the melting range. The exact temperatures depend on the glass composition but may be between 400° C to 1200° C. In the case of the EJ glass composition described in EP1 154443 the sinter temperature is between 720° C. and 770° C., preferably around 750° C. It is in the skill of the artisan to find out the temperatures for each glass composition when taking the teachings of the present invention into account. Afterwards, the powder is heated for 1 hour to 200° C., optionally cooled to room temperature and heated to 750° C. (densification or sinter temperature) in a nitrogen atmosphere with a heating rate of 1 K/min and is held at that temperature for 1 hour. Then the furnace is cooled to 150° C. and heated again to 200° C. for one hour in air. After the cooling to room temperature, the powder is transferred to a sieve (50 µm) and sieved for 30 min. The sieved sample is bottled and sterilized at 200° C. for 4 h and then cooled to 80° C. Then the glass vessels are taken from the oven, covered with sterile foil and closed.

Preferably the method according to the invention is used in diagnostics, for diagnostic analysis or for bioanalytics, or for the screening of fluids from the human or even animal body for the presence of a target nucleic acid, i.e. for example a nucleic acid from a virus. Further, the method according to the invention is used to enhance the speed, accuracy or sensitivity of the detection of a target nucleic acid.

The following examples, references and figures are provided to aid the understanding of the present invention, the true scope of which is set forth in the appended claims. It is understood that modifications can be made in the procedures set forth without departing from the spirit of the invention.

EXAMPLES

Example I

Influence of Magnetic Glass Particles (MGPs) on a TAQ-MAN® PCR

The example describes experiments carried out to measure the effect of magnetic glass particles (MGP) on amplification efficiency. The amplifications were carried out using a TAQ-MAN® PCR protocol, as described below.

In a TaqMan assay, labeled detection probes that hybridize within the amplified region are added to the amplification reaction mixture. The probes preferably are modified so as to prevent the probes from acting as primers for DNA synthesis. Amplification is carried out using a DNA polymerase that possesses 5' to 3' exonuclease activity, e.g., Z05 DNA polymerase. During each synthesis step of the amplification, any probe which hybridizes to the target nucleic acid downstream from the primer being extended is degraded by the 5' to 3' exonuclease activity of the DNA polymerase. Thus, the synthesis of a new target strand also results in the degradation of a probe, and the accumulation of degradation product provides a measure of the synthesis of target sequences.

The increase of amplification products during a TAQ-MAN® reaction can be monitored using fluorescent probes. The detection probes are labeled with two fluorescent dyes, one of which is capable of quenching the fluorescence of the other dye, such that the probes are self-quenching when in proximity to one another, i.e. when bound to the same probe or nucleic acid. The dyes are attached to the probe, preferably one attached to the 5' terminus and the other attached to an internal site, such that cleavage of the probe by the 5' to 3' exonuclease activity of the DNA polymerase occurs in between the two dyes.

Amplification results in cleavage of the probe and separation of the dyes, with a concomitant elimination of quenching and increase in the fluorescence observable. Thus, the accumulation of degradation product, which is a measure of the increase in amplification product, is monitored by measuring the increase in reaction fluorescence.

In the experiments described in this example, each probe was synthesized to contain a polymethine-cyanine dye and a 6-carboxy-fluorescein label. The resulting probes are self-quenching when in proximity to one another. To prevent extension of the probe by the DNA polymerase during the amplification, the probe was synthesized with a 3' phosphate block. The accumulation of amplified product was measured at each cycle during the reaction by measuring the increase in reaction fluorescence. During each amplification cycle, the probes were excited with light at a wavelength near the excitation maximum of the fluorophore and the emission of the fluorophore was measured near its emission maximum.

Fluorescence measurements were normalized by dividing by an initial fluorescence measurement, i.e., the background fluorescence, obtained during a cycle early in the reaction while the fluorescence measurements between cycles appear to be relatively constant. The cycle number chosen for the initial fluorescence measurement was the same for all reactions compared, so that all measurements represent increases relative to the same reaction cycle.

In the early cycles of a polymerase chain reaction amplification, the number of target molecules can be described by the geometric equation $$N_i = N_o \times (1+E)^i,$$

where $N_i$=the number of target molecules at the completion of the ith cycle, $N_o$=the number of target molecules at the start of the reaction, and E=the efficiency of the amplification (0=<E=<1). During this geometric growth phase of the amplification, the number of cycles required to reach a particular threshold value ($C_T$) is inversely proportional to the logarithm of (1+E). Thus, the $C_T$ value represents a measure of the reaction efficiency that allows comparisons between reactions. A decrease in the $C_T$ value, which means that the reaction reached the threshold value in fewer cycles, indicates an increase in overall sensitivity.

As the increase in amplification product is monitored by measuring the increase in reaction fluorescence, the $C_T$ is defined herein as the number of amplification cycles carried out until the fluorescence exceeded an arbitrary fluorescence level (AFL). The AFL was chosen close to the baseline fluorescence level, but above the range of random fluctuations in the measured fluorescence, so that the reaction kinetics were measured during the geometric growth phase of the amplification. Accumulation of amplified product in later cycles inhibits the reaction and eventually leads to a reaction plateau.

An AFL of 1.5 was chosen for all reactions. Because a PCR amplification consists of discrete cycles and the fluorescence measurements are carried out once per cycle, the measured fluorescence typically increases from below the AFL to above the AFL in a single cycle. To improve the precision of the measurements, an "exact" number of cycles to reach the AFL threshold, referred to herein as the $C_T$ value, was calculated by interpolating fluorescence measurements between cycles.

Reaction Conditions

Reactions were carried out using the reaction components shown below. Each test was done in a threefold assay.

| test 1: | 25.75 µl Mastermix component R1 |
| | 24.25 µl Mastermix component R2 |
| | 50 µl HCV standard material (diluted in poly A solution) |
| test 2: | 25.75 µl MasterMix component A |
| | 24.25 µl MasterMix component B |
| | 50 µl HCV standard material (diluted in poly A solution) |
| | 6 mg Magnetic Glass Particles ("Cerac" MGP, as described above) |

Formulation of Mastermix Component R1 and R2:

| Contents | Concentration of the stock solution | Final concentration in reaction | µl/reaction | µl/reaction/$R_i$ |
|---|---|---|---|---|
| R1 | | | | |
| Pure water | | | 10.85 | |
| Mn(Ac)$_2$ pH = 6.5 | 50 mM | 3 mM | 6.00 | |
| KOAc pH = 7.0 | 2 M | 100 mM | 5.00 | |
| Glycerol (free) | 80% | 2.8% | 3.50 | |
| HCV probe ST650p2 | 50 µM | 10 pmol/100 µl | 0.20 | |
| IC probe ST2535Cy5F15 | 50 µM | 10 pmol/100 µl | 0.20 | 25.75 |
| R2 | | | | |
| Primer 1(HCV) ST280A | 50 µM | 15 pmol/100 ml | 0.30 | |
| Primer 2(HCV) ST778AA | 50 µM | 40 pmol/100 µl | 0.80 | |
| Tricine pH = 8.3 | 1 M | 50 mM | 5.00 | |
| dNTPs, not equimolar (GAC) | 100 mM | 300 µM | 2.50 | |
| dNTPs, not equimolar (T) | 100 mM | 50 µM | | |
| dNTPs, not equimolar (U) | 100 mM | 500 µM | | |
| ZO5 Polymerase | 10 U/µl | 40 U/100 µl | 4.00 | |
| Uracil N glycosylase (UNG) | 2.0 U/µl | 10 U/100 µl | 5.00 | |
| Dimethylsulfoxide DMSO | 80% | 5% | 6.25 | |
| NTQ21-46A | 50 µM | 20 pmol/100 µl | 0.40 | 24.25 |

The sequences of primers ST280A and ST778AA are described in U.S. Pat. No. 5,837,442. The 3' terminal nucleotide of each primer was modified by the covalent attachment of a p-tert-butylbenzyl group to the 3' terminal nucleotide, as described in European Patent Application No. 866,071 and U.S. Pat. No. 6,001,611.

The sequences of the HCV-specific probe and the internal control (IC)-specific probes are provided below in the 5' to 3' orientation. HCV-specific probes were synthesized to contain a Cy5 fluorophore attached to the 5' terminus through the terminal phosphate using a commercially available phosphoramidite (Pharmacia, Piscataway, N.J.). A 6-carboxyfluorescein (FAM) label was incorporated in an internal position between nucleotides 14 and 15 using a labeled linker commercially available as a phosphormaidite from BioGenex (San Ramon, Calif.). The resulting probes are self-quenching when in an unhybridized state. To prevent extension of the probe by the DNA polymerase during the amplification, the probe was synthesized with a 3' phosphate block using a phosphoramidite commercially available from Glenn Research (Sterling, Va.).

HCV probe ST650p2:
(Cy5-) CGG TGT ACT CAC CG(FAM) TTC CGC AGA CCA CTA TG  (SEQ ID NO: 1)

IC probe ST2535Cy5F15:
(Cy5-) TGG ACT CAG TCC T(HEX)T GGT CAT CTC ACC TTC T  (SEQ ID NO: 2)

The following oligonucleotide was included in reaction mixture R2 to inhibit DNA polymerase activity at low temperatures.

NTQ21-46A                                    (SEQ ID NO: 3)
CGA TCA TCT CAG AAC ATT CTT AGC GTT TTG TTC TTG
TGT ATG ATC G

HCV standard material consisted of HCV RNA templates synthesized using an HCV RNA transcription vector essentially as described in Young et al., 1993, J. Clin. Microbiol. 31(4):882-886. The HCV RNA templates were diluted in poly A solution (20µg/ml Poly rA, 10 mM Tris-HCl pH8.0, 0.1 mM EDTA, 0.05% Sodium azide, DEPC treated water, filtrated sterile) to a concentration of 200 copies per 50 µl.

Amplification Protocol

Amplifications were carried out using the following temperature profile:

| | |
|---|---|
| Pre-reaction incubation | 45° C., 10 minutes |
| Initial denaturation | 94° C., 30 seconds |
| Reverse transcription | 58° C., 30 minutes |
| 5 Cycles | 95° C., 20 seconds; 59° C., 50 seconds |
| 55 Cycles | 91° C., 15 seconds, 52° C., 50 seconds |

Results

Figure 2:
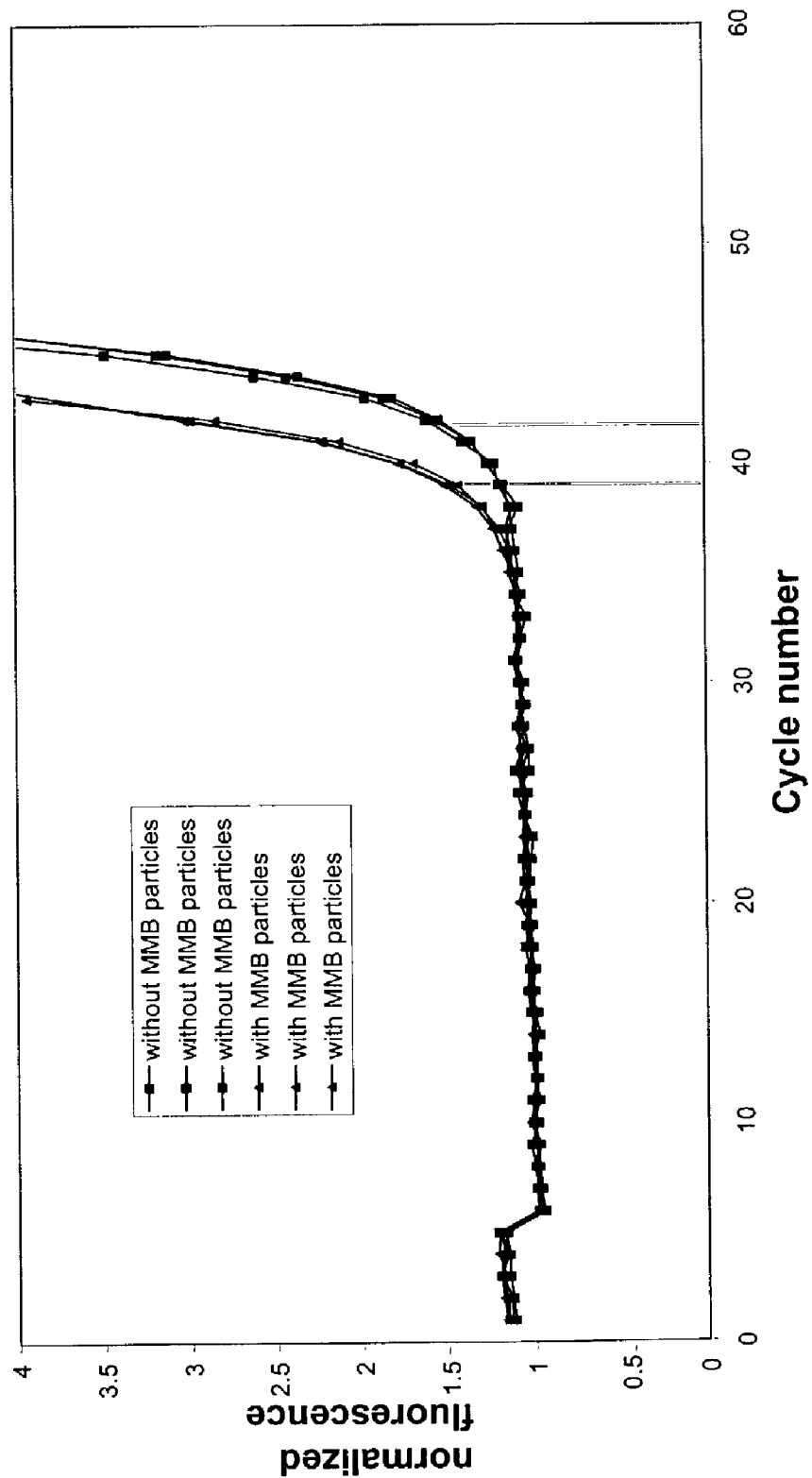
FIG. 2: Comparison of the $C_T$-values of PCR reactions with and without magnetic glass particles containing the MMB pigment (Merck) (cp/ml: copies/ml).

The results of the reactions are provided in FIGS. 1 and 2. The $C_T$ values are indicated for each reaction. Comparing the $C_T$ values, it is apparent that the reactions carried out in the presence of magnetic glass particles reached the threshold value earlier that the comparable reactions carried out without the magnetic glass particles in the reaction. These results demonstrate the surprising increase in reaction efficiency obtained by carrying out the amplification in the presence of the magnetic glass particles.

LIST OF REFERENCES

Abramson and Myers, Current Opinion in Biotechnology 4 (1993)41-47
Anal. Biochem. 121 (1982) 382-387
Anal. Biochem. 175 (1988) 196-201
Anal. Biochem. 201 (1992) 166-169
Analytical Biochemistry 175 (1988) 196-201
Andreadis and Chrisey (2000). Nucl. Acids Res. Vol. 28, No. 2, eS, I-VIII.
Ausubel, et al., Current Protocols in Molecular Biology (1987), J. Wiley and Sons, NY, USA
Barany, PCR Methods and Applic. 1 (1991)5-16
Barany, Proc. Natl. Acad. Sci. USA 88 (1991)189-193
C. J. Brinker, G. W. Scherer, Sol Gel Science—The Physics and Chemistry of Sol Gel Processing, Academic Press Inc. (1990)
Chungue et al. (1993) J. Med. Virol. 40, 142-145.
DE 198 54 973.3
DE 198 55 259.9
DE 3724442
DE198 01 730
DE198 16 137
DE-A 37 34 442
DE-A-1941191
DE-A-3719339
DE-A-4117041
DE-A-4217432
Eberwine, BioTechniques 20 (1996) 584-591
EP 00110165.8
EP 439,182 A2
Guatelli, et al., Proc. Natl. Acad. Sci. USA 87 (1990)1874-1878
Kwoh, et al., Proc. Natl. Acad. Sci. USA 86 (1989)1173-1177
Lisa C. Klein, Ed., Kluwer Academic Publishers (1994) 450 ff.
Lottspeich and Zorbas (eds.), "Bioanalytik" (1st edition 1998), Spektrum Akademischer Verlag, Heidelberg, Berlin, Germany
Masters: Spray Drying Handbook, Fifth Edition, John Wiley & Sons (1991) New York
Orum, et al., Nucl. Acids Res. 21 (1993) 5332-5336
PCT GB 91/00212
S. Braunauer, The Adsorption of Gases and Vapors, Princeton University Press 1 1943
Sambrook, et al., Molecular Cloning, Cold Spring Harbor University Press (1989)
Seeger, et al., BioTechniques 23 (1997) 512-517
Tano, et al., J. Clin. Microbiol. (1995)
U.S. Pat. No. 4,683,195
U.S. Pat. No. 5,130,238
U.S. Pat. No. 5,210,015
U.S. Pat. No. 5,487,972
U.S. Pat. No. 5,804,375
Whelen and Persing, Annu. Rev. Microbiol. 50 (1996) 349-373
WO 00/32762
WO 90/01069
WO 92/02638
WO 92/0880A
WO 96/41811
WO 99/16781
WO 99/40098
Wu and Wallace, Genomics 4 (1989)560-569

Various embodiments of the invention have been described. The descriptions and examples are intended to be illustrative of the invention and not limiting. Indeed, it will be apparent to those of skill in the art that modifications may be made to the various embodiments of the invention described without departing from the spirit of the invention or scope of the appended claims set forth below.

All references cited herein are hereby incorporated by reference in their entireties.

---

---

We claim:

1. A method for the purification and amplification of a target nucleic acid from a biological sample comprising said target nucleic acid, said method comprising the steps of:
   a) adding a material comprising magnetic glass particles with an unmodified silica surface to said sample to bind said target nucleic acid to said material,
   b) separating said material from said sample,
   c) eluting said target nucleic acid from said material, and
   d) amplifying said target nucleic acid in the presence of at least 50% of the material added in step a), wherein said target nucleic acid is detected during amplification and wherein said magnetic glass particles are manufactured by the sol-gel method.

2. The method of claim 1, wherein said target nucleic acid is RNA or DNA.

3. The method of claim 1, wherein said step of amplifying is performed using a polymerase chain reaction.

4. The method of claim 1, wherein said material comprising an unmodified silica surface is present while amplifying the target nucleic acid and while detecting the amplified target nucleic acid.

5. The method of claim 1, wherein said material comprises glass beads with an unmodified glass surface.

6. The method of claim 1, wherein said sol-gel method comprises the steps of
   a) suspending magnetic objects in a sol,
   b) hydrolyzing the sol to cover the magnetic objects with a gel,
   c) spray-drying the magnetic objects covered with a gel in a two-nozzle spray-drier, and
   d) sintering the spray-dried powder to form a glass from the gel covering the magnetic objects.

7. The method of claim 6, wherein the inlet temperature of the two-nozzle spray-drier is between 120° C. and 500° C., the outlet temperature is chosen according to the boiling point of the sol and the spray pressure is between 4 and 6 bar.

8. The method of claim 7, wherein the half-life period for the sedimentation of a 3 mg/ml weight-per-volume suspension of the magnetic glass particles in isopropanol is more than 6 minutes.

9. The method of claim 7, wherein the magnetic glass particles have a mean diameter between 0.5 µm and 5 µm.

10. The method of claim 7, wherein the magnetic glass particles with an unmodified glass surface contain a magnetic object with a diameter between 5 and 500 nm.

11. The method of claim 7, wherein the magnetic glass particles with an unmodified glass surface contain a magnetic object with a mean diameter of 23 nm.

* * * * *

SEQUENCE LISTING

```
<160> NUMBER OF SEQ ID NOS: 3

<210> SEQ ID NO 1
<211> LENGTH: 31
<212> TYPE: DNA
<213> ORGANISM: Artificial
<220> FEATURE:
<223> OTHER INFORMATION: HCV specific probe

<400> SEQUENCE: 1
cggtgtactc accgttccgc agaccactat g                                   31

<210> SEQ ID NO 2
<211> LENGTH: 30
<212> TYPE: DNA
<213> ORGANISM: Artificial
<220> FEATURE:
<223> OTHER INFORMATION: Internal Control Specific Probes

<400> SEQUENCE: 2
tggactcagt ccttggtcat ctcaccttct                                     30

<210> SEQ ID NO 3
<211> LENGTH: 46
<212> TYPE: DNA
<213> ORGANISM: Artificial
<220> FEATURE:
<223> OTHER INFORMATION: DNA Polymerase  activity inhibitor at low
      temperatures

<400> SEQUENCE: 3
cgatcatctc agaacattct tagcgttttg ttcttgtgta tgatcg                   46
```